United States Patent [19]

Kurakake et al.

[11] Patent Number: 5,771,512
[45] Date of Patent: Jun. 30, 1998

[54] NUCLEAR IMAGE DIAGNOSIS APPARATUS HAVING PATIENT ARM AND HEAD SUPPORT

[75] Inventors: Tadakazu Kurakake; Toshiro Iwasaki, both of Tochigi-ken, Japan

[73] Assignee: Kabushiki Kaisha Toshiba, Kawasaki, Japan

[21] Appl. No.: 815,904

[22] Filed: Mar. 12, 1997

Related U.S. Application Data

[63] Continuation of Ser. No. 527,726, Sep. 13, 1995, abandoned.

[30] Foreign Application Priority Data

Sep. 20, 1994 [JP] Japan .................................. 6-225063

[51] Int. Cl.$^6$ .................................................. A47C 1/036
[52] U.S. Cl. ........................... 5/623; 5/601; 5/621; 5/622
[58] Field of Search .............................. 5/601, 623, 624, 5/622; 378/621, 208, 209

[56] References Cited

U.S. PATENT DOCUMENTS

| | | | |
|---|---|---|---|
| 4,045,678 | 8/1977 | Rickard | 378/208 |
| 4,484,571 | 11/1984 | Velazquez | 5/601 |
| 4,506,872 | 3/1985 | Westerberg et al. | 378/209 |
| 4,681,308 | 7/1987 | Rice | 5/601 |
| 4,698,837 | 10/1987 | Van Steenburg | 5/601 |
| 4,836,523 | 6/1989 | Englander . | |
| 5,014,292 | 5/1991 | Siczek et al. | 378/208 |
| 5,020,089 | 5/1991 | Cramer et al. | 378/209 |
| 5,090,044 | 2/1992 | Kobayashi | 378/209 |
| 5,199,060 | 3/1993 | Kato | 378/208 |
| 5,490,296 | 2/1996 | Fleury et al. | 5/601 |

*Primary Examiner*—Rodney M. Lindsey
*Assistant Examiner*—Frederick Conley
*Attorney, Agent, or Firm*—Oblon, Spivak, McClelland, Maier & Neustadt, P.C.

[57] ABSTRACT

An apparatus for image diagnosis including an arm rest device having support surfaces for supporting a patient's upheld arms without the use of grasping handles during image diagnosis while the patient is placed in a supine position. The apparatus includes a table on which the patient can be placed, a table support for supporting the table, a detector device for detecting radiation emitted from a radiation source passing through the patient in order to reconstruct cross sectional images of the patient, a gantry for carrying the detector to an investigating position, and the arm rest device. The arm rest device includes a U-shaped base member which has a fixing guide for mounting the arm rest device on the table support and a pair of arm rest pad members which are adjustably placed in the U-shaped base member at appropriate positions for supporting the patient's upheld arms. The arm rest pad members have triangular cross sections defining different interior angles and can be selectably arranged to provide support surfaces at different angles of inclination.

42 Claims, 10 Drawing Sheets

NUCLEAR IMAGE DIAGNOSIS APPARATUS HAVING PATIENT ARM AND HEAD SUPPORT

This is a Continuation of application Ser. No. 08/527,726, filed on Sep. 13, 1995, now abandoned.

BACKGROUND OF THE INVENTION

1. Field of the Invention

This invention relates to an apparatus for image diagnosis.

In particular, this invention relates to an image diagnosis apparatus including a novel detachable arm rest device.

More particularly, this invention relates to an improvement in an image diagnosis apparatus in which diagnosis accuracy is easily affected by the patient movement.

This invention further relates to an image diagnosis apparatus having a novel arm rest device for patient comfort and which avoids undesirable artifacts in the reconstructed images due to patient movement during image diagnosis.

This invention further relates to an image diagnosis apparatus having a novel detachable arm rest device including arm resting pad members for easily changing pad positions and inclination angles to adjust to a patient's physical conditions.

This invention further relates to an image diagnosis apparatus having a novel detachable arm rest device which can keep patient posture still while the patient holds his hands beside his head for a long time without requiring the patient to grab any handles or posts.

DISCUSSION OF BACKGROUND

During image diagnosis using an image diagnosis apparatus, for example, a scintillation camera apparatus, the patient must be placed on a table top of the apparatus in a supine position while holding his arms and hands besides his head for a long time for the image diagnosis.

For making the image diagnosis, it is usually necessary to obtain a lot of transverse sectional images of the patient body. The transverse sectional images are obtained by rotating a detector device around the patient body and detecting investigation rays transmitted through the patient at various angles.

In particular, it usually takes more than a half hour to the necessary number of images for a cardiac radiography image diagnosis by using a scintillation camera apparatus. During such a long time the patient must keep still with arms and hands besides the head in order to obtain accurate transverse sectional images without any artifacts, i.e., false images detected by the detector device due to the movement of the patient. Such artifacts cause a serious misunderstanding and erroneous medical diagnosis.

In case of the scintillation camera image diagnosis apparatus, the radiation source is an injected radioisotope into the patient body. Accordingly, the movement of the patient during the image diagnosis causes artifacts to appear. Recently, a single photon emission computed tomography (hereinafter refers to SPECT) scintillation camera apparatus has been developed to obtain much higher resolution images of the distribution of the radioisotope through the patient's body.

The detector device of the SPECT scintillation camera apparatus is precisely positioned as close as possible to the anatomy under investigation in order to increase the resolution of the detected images.

Particularly, in case of a cardiac image diagnosis, it is necessary to obtain many transverse sectional images of the patient's body, usually exceeding several tens to hundreds of images or more.

The SPECT scintillation camera apparatus obtains the image information by rotating the detectors device around the cardiac part of the patient's body as close as possible along an elliptical orbit or a random orbit.

During the cardiac image diagnosis, the patient must keep still in order to obtain high resolution images without any undesirable radiography artifacts due to the patient's movement.

Since the patient must keep still arms and hands beside his head for a long time during the cardiac image diagnosis, the patient becomes very exhausted and feels stress or fatigue during the time for the cardiac image diagnosis.

As mentioned before, the SPECT scintillation camera apparatus increases the image resolution, but detects erroneous artifacts when the patient moves his body or arms due to fatigue during the image diagnosis.

Accordingly, it is necessary to take some measure for avoiding patient stress or fatigue and for keeping the patient more comfortable during the image diagnosis.

U.S. Pat. No. 4,836,523, issued Jun. 6, 1989 to Englander teaches providing a hand grips attachment in the form of inverted U-shaped steel handles for the patient to grab during a medical operation. While the Englander patent intends to relieve the patient's stress and to make the patient more comfortable during the surgical operation, such a proposed hand grip device can hardly avoid patient fatigue during lengthy cardiac image diagnosis since the patient must keep grabbing the post handle tightly during the entire medical operation. Such a grasping handle device is not applicable for a cardiac image diagnosis apparatus because the patient becomes very exhausted and feels stress and fatigue during the long cardiac image diagnosis investigation.

SUMMARY OF THE INVENTION

Accordingly, one object of the present invention is to solve the above-mentioned problems and defects causing by patient fatigue due to grasping the handle device for a long time during image diagnosis.

Another object of this invention is to avoid erroneous diagnosis caused by the appearance of artifacts in the images reconstructed by the image diagnosis apparatus.

Still another object of the present invention is to provide an apparatus for image diagnosis having a novel patient arm rest device detachably mounted to a support member of the top table of the apparatus, whereby the patient's arms can be supported without the use of grasping handles during a lengthy image diagnosis.

Another object of this invention is to provide an apparatus for image diagnosis including a detachable patient's arm rest device including arm rest pad members for comfortable support of the patient's arms while the patient maintains a still posture, while resting his arms on the arm rest pad members, during a lengthy image diagnosis.

A further object of this invention is to provide an apparatus for image diagnosis including a detachable patient's arm rest device including arm rest pad members having changeable position and inclination depending upon the patient's physical condition.

Still further an object of this invention is to provide an apparatus for image diagnosis including a detachable patient arm rest device having arm rest pad members fixed at an appropriate position or at preferable angles for leaning support of the patient's arms depending upon the patient's condition.

Still another object of this invention is to provide an apparatus for image diagnosis including a detachable patient arm rest device having arm rest pad members for a supporting patient's arms and an additional head fixing for supporting the patient's head.

These and other objects are achieved according to the present invention by providing a novel image diagnosis apparatus including a table for placing a patient, a table support means for supporting the table, a detector device for detecting radiation emitted from a radiation source passing through the patient body in order to reconstruct cross sectional images of the patient body, a gantry for carrying the detector device to an investigating position relative to the patient body, and an arm rest device including an U-shaped base member which has at least one fixing device for mounting to the table support and a pair of arm rest pad members adjustably placed in the U-shaped base member at an appropriate position for supporting the patient's upheld arms depending upon the patient's physical condition.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1 and 2 are perspective views of a scintillation camera apparatus on which a patient is placed on a top table of the apparatus in a supine position with the patient's arms resting on the novel patient arm rest device means, wherein FIG. 1 shows an initial stage of image diagnosis at which the detector device of the apparatus is positioned at a gantry home position and the table plate is lowered by an elevator in the table support stand to facilitate getting the patient on and off the table plate, and FIG. 2 illustrates an actual image diagnosis stage at which the detector is moved to the SPECT position for the patient's body by moving and rotating the detector device on the gantry along the patient body lying on the table plate;

FIGS. 5(a) to 5(d) are illustrations of a U-shaped guide portion of the patient arm rest device, wherein.

FIGS. 6(a) and 6(b) depict one example of a mat portion to be placed in the guide portion of the patient arm rest device, wherein.

FIGS. 7 to 9 illustrates various uses of the patient's arm rest device in dependence upon the patient's condition in which one of the guide portions is omitted for a better understanding, wherein

DETAILED DESCRIPTION OF THE PREFERRED EMBODIMENTS

To provide a basis for a discussion of the apparatus of the present invention, a brief explanation of the image diagnosis apparatus of the SPECT type scintillation camera in which the patient is placed in a supine position on the top plate of the apparatus is provided. However, it should be understood that the present invention is applicable to any type of image diagnosis apparatus, for example, a nuclear image diagnosis apparatus, like a scintillation camera apparatus or a nuclear magnetic resonance apparatus and also to an X-ray computer tomography apparatus.

For a simplified understanding of the present invention, the following explanation of an exemplative embodiment is provided in the context of a scintillation camera apparatus.

Figure 1:
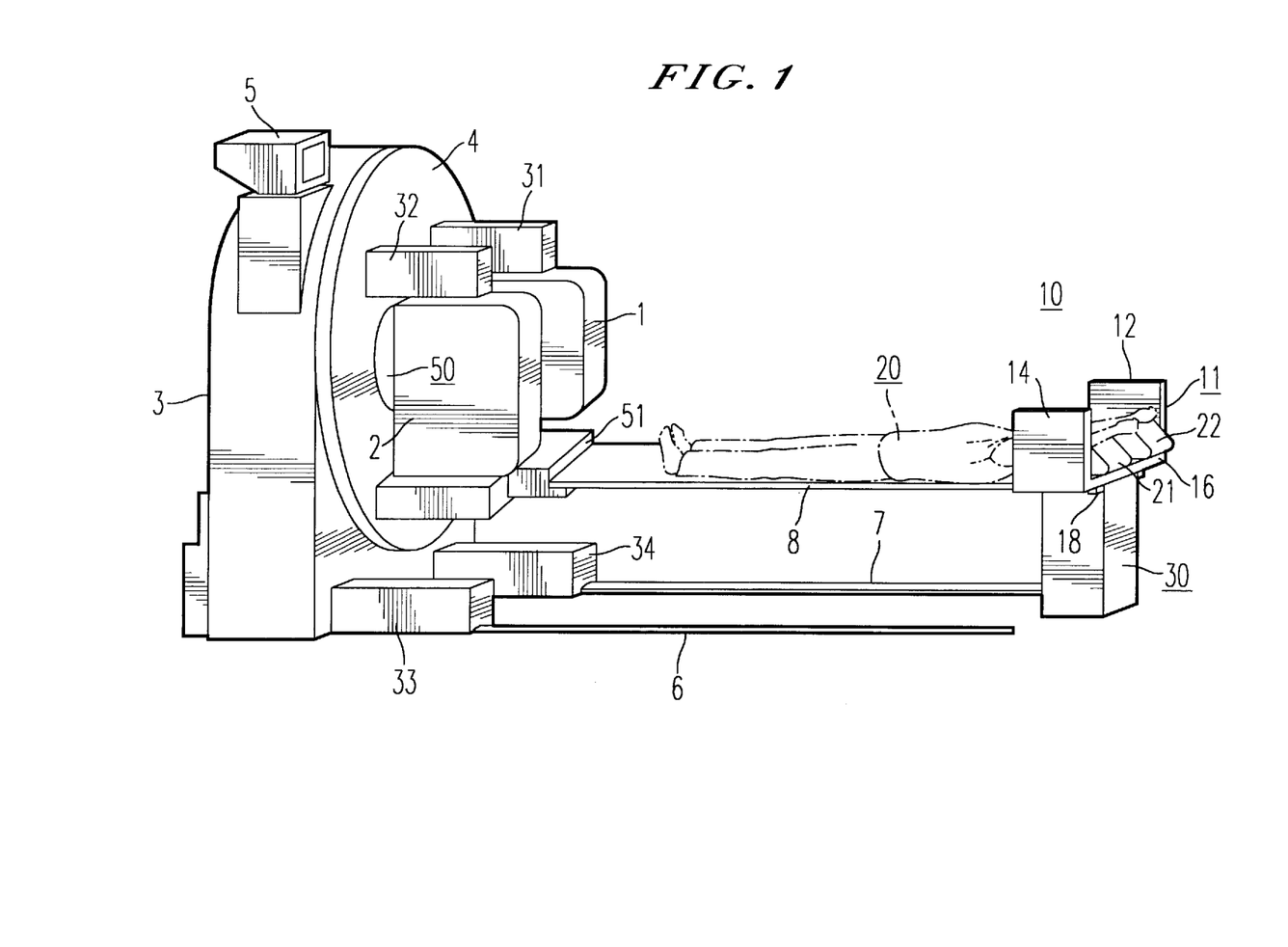
Figure 2:
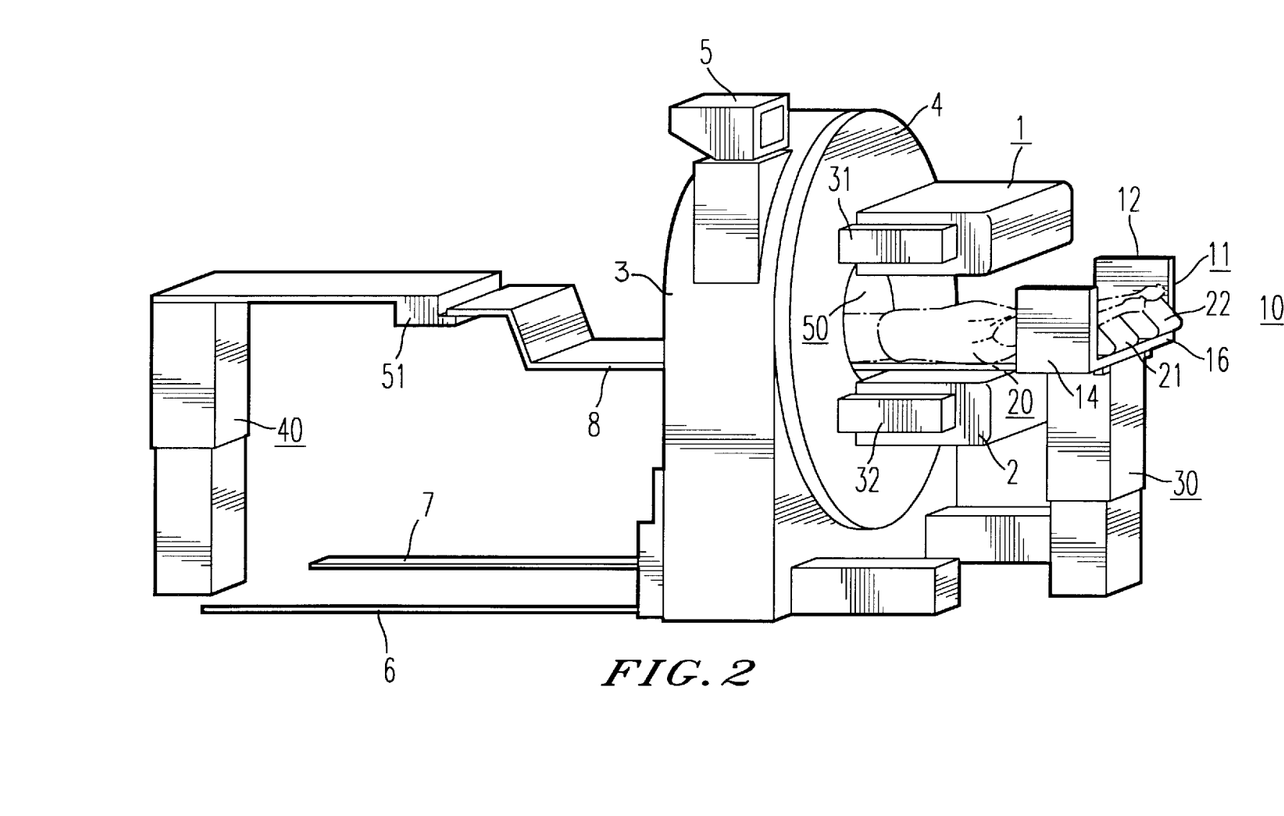

Referring to the drawing where like reference numerals refer to identical or corresponding parts throughout the several views, there is shown in FIGS. 1 and 2 a scintillation camera apparatus on which a patient is placed in a supine position while accommodating his arms and hands on a novel arm rest device attached at one end of the top plate of the apparatus.

As explained above, FIG. 1 shows an initial status before beginning the image diagnosis. At the initial stage, the gantry 3 for the detector devices 1 and 2 of the image diagnosis apparatus 10 are at a home position and the top table 8 is elevated at its lowest position by an elevator in the table support stand 30 for easily putting the patient on the table 8.

FIG. 2 illustrates an image diagnosis stage at which the detector devices 1 and 2 are carried to a SPECT diagnosis position to the patient body 20 by moving the gantry 3 along the table 8.

In FIGS. 1 and 2, a pair of detector devices 1 and 2 are supported on a rotating device 4 of a gantry 3 on which a monitor TV 5 is positioned for imaging the emitted γ rays from the patient body 20 on the screen in real time for confirming the detector positions against the patient body 20 on the table 8.

The detector devices 1 and 2 are respectively attached to the rotating device 4 by a pair of support members 31 and 32.

The gantry 3 is automatically slidable on the parallel rails 6 and 7 along the table plate 8 passing through the central aperture 50 of the gantry 3.

In FIG. 2, the gantry 3 is carried to a SPECT position for the patient body 20, and the pair of detector devices 1 and 2 are rotating to obtain image information from the patient body 20.

The table 8 is elevated to a higher position for ease of diagnosis. A pair of table support stands 30 and 40 are shown, and the gantry 3 carries and rotates the detector devices 1 and 2 around the SPECT position of the patient body 20.

During the image diagnosis, the patient is placed on the table 8 in a supine position while upholding his arms and hands besides his head as shown in FIGS. 1 and 2. The patient places his arms and hands on an arm rest device 10 which is detachably mounted on one of the table support stands 30.

The arm rest device 10 includes a U-shaped base member 11 and a pair of arm rest pad members 22. The U-shaped base member 11 includes a pair of side walls 12 and 14 and a base plate 16. The detailed structure of the arm rest device 10 will be explained later.

Figure 3:
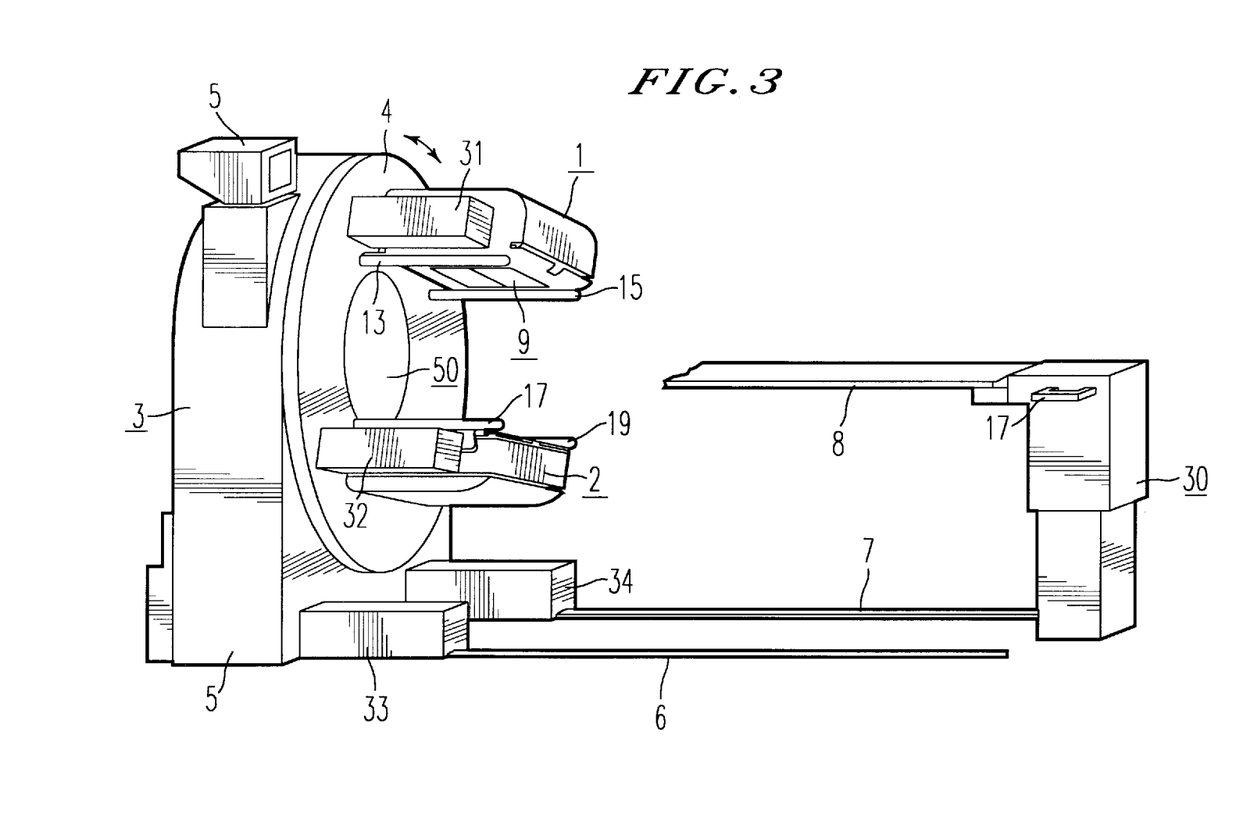
FIG. 3 is a partially cut off perspective view of a scintillating camera apparatus in which the patient's arm rest device is removed from the plate stand.

FIG. 3 shows the arrangement of the detector devices 1 and 2, the table plate 8 and the support stand 30 with the arm rest device 10 detached from the table support stand 30.

As shown in FIG. 3, the detector device 1 includes a light source 13 and a light receiving sensor 15 and a γ-ray detecting window 9 provided between the light source 13 and the sensor 15. The detector 2 has the same structure as the detector 1, including a light source 17 and a light receiving sensor 19.

As shown in FIG. 3, the table support stand 30 has a stopper 17 for fixing the arm rest device 10. Of course, various kind structures can be used for the stopper 17, the stopper 17 being only one example of a plate type stopper projected from the table support stand 30.

For example, instead of the stopper 17 shown in FIG. 3, also applicable are an interfitting groove device, a band fixing device, or a slide plate fixing device.

The detailed structure and examples of how to use the patient arm rest device 10 are next explained with reference FIGS. 4 through 10.

Figure 4:
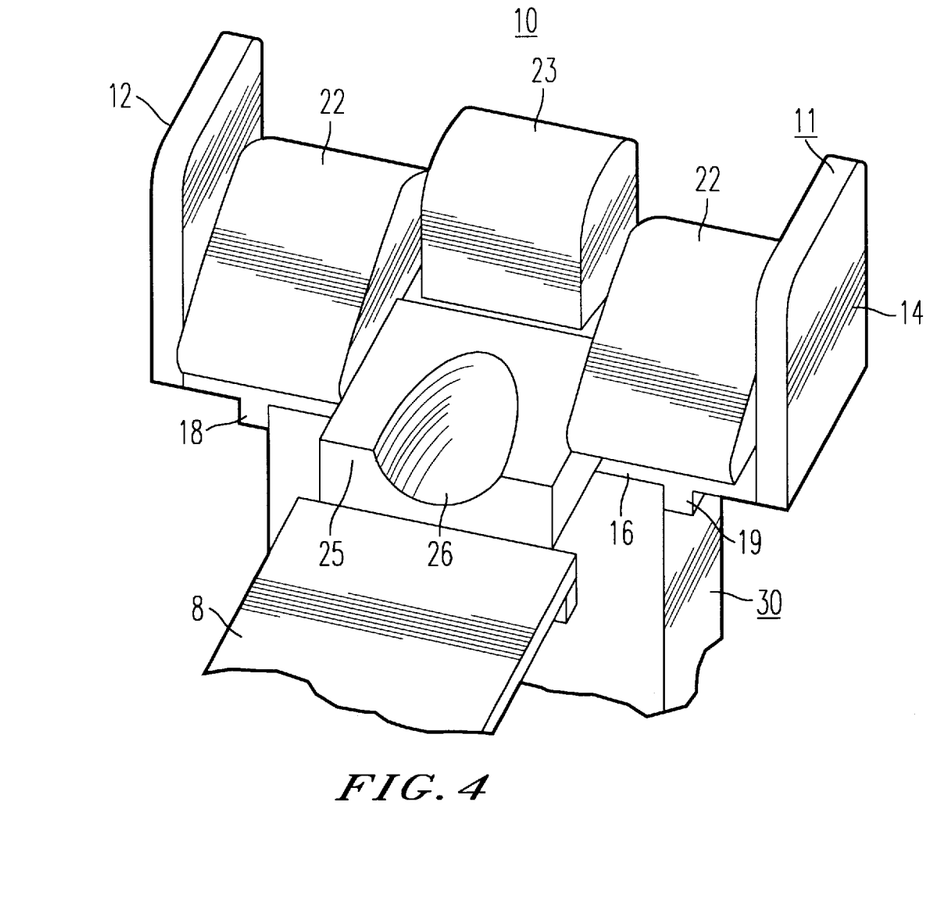
FIG. 4 is a detailed perspective view of the novel patient arm rest device which is attached on the top plate support stand of the image diagnosis apparatus.

Referring first to FIG. 4, the arm rest device 10 includes at least a side wall member 12 and an arm rest pad member 22 which are detachably mounted on the table support stand 30, for providing rest surfaces for the patient's arms without grasping handles during the time for image diagnosis while the patient is placed on the table 8 in a supine position while upholding his arms besides his head.

In FIG. 4, the arm rest device 10 includes a U-shaped guide member 11 including a pair of side walls 12 and 14 and a base plate 16 which has a pair of projected leg members 18 for attaching the arm rest device 10 to the table support stand 30.

The base plate 16 supports the side walls 12 and 14 and also includes at least one fixing guide member 18 for mounting the arm rest device 10 on the table support stand 30. In FIG. 4, the table 8 and the table support stand 30 are partially shown.

The pair of side walls 12 and 14 of the U-shaped base member 11 are shown as vertically arranged. It is, of course, possible to slightly tilt the wall outward or inward.

At least one arm rest pad member 22, and typically a pair of arm rest pad members 22, are adjustably fitted on the base plate member at appropriate positions between the pair of side walls 12, 14 for resting support of the patient's upheld arm(s) depending upon the patient's physical condition.

In the example in FIG. 4, the pair of arm rest pad members 22 are adjustably positioned between the pair of side walls 12 and 14 in order to match the patient's arm position depending upon the patient's arm condition.

The U-shaped base member 11 and the pair of arm rest pad members 22 are preferably at least partially made of soft material, like an urethane foam for supporting the patient's arms and hands.

The U-shaped base member includes at least one fastener for fixing the arm rest pad members 2 on the base plate 16 at appropriate positions depending upon the patient's physical condition.

As an example shown in FIG. 5(*b*), the U-shaped base member 11 includes three fasteners 42, 44 and 46 arranged H-shaped for fixing the pair of arm rest pad members 22 and a head seat member 25 shown in FIG. 4.

Figure 5A:
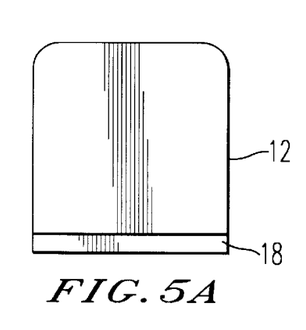
FIG. 5(a) is a side view of the guide portion of the patient arm rest device.
Figure 5B:
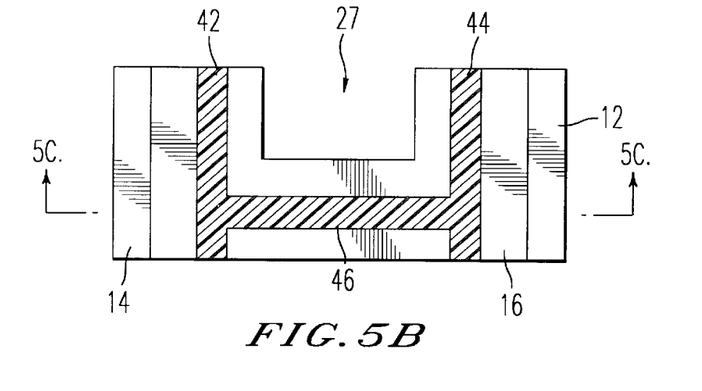
FIG. 5(b) is a top view of the guide portion of the patient arm rest device.
Figure 5C:
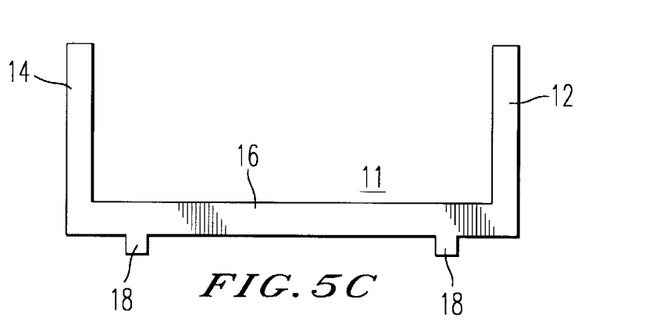
FIGS. 5(c) and 5(d) are cross sectional views of the guide portion of the patient arm rest device, taken along the A—A dotted line in FIG. 5(b), respectively.
Figure 5D:
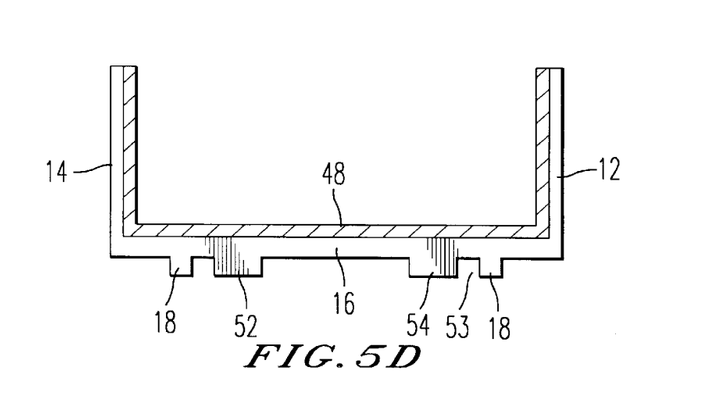

Referring again to FIG. 4, the head seat member 25 is provided between the pair of the arm rest members 22 for sitting the patient's head. The base plate 16 has cutout portion 27 (See FIG. 5(*b*)) for positioning the head seat member 25.

The arm rest device 10 further includes a head fixing member 23 provided between the pair of arm rest pad members 22 so as to fix the patient's head into the head seat member 25.

It is possible to make the pair of arm rest pad members 22 and the head fixing member 23 as a U-shaped one piece member.

The base plate 16 of the U-shaped base member 11 includes an H-shaped fastener 42, 44, 46 for securing both the head fixing member 23 and the pair of arm pad members 22.

The head seat member 25 has a central head fitting depression 26 which preferably made of a urethane foam.

The head fixing member 23 is preferably higher than the arm rest pad members 22 for putting the patient's hands on it.

A flat surface fastener is used to fasten the base plate 16 and at least one surface of the respective arm rest pad member 22 for interfitting with each other in order to fix the pad members 22 at appropriate positions.

It is possible to provide fasteners on additional surfaces surrounding the pad member in order to selectably fasten the patient arm rest device 10 with an optional inclination.

FIG. 5(*a*) is a side view of one example of the base member 11 of the arm rest device 10, which includes a vertical side wall member 12 and a projected leg member 18 for fixing to the table support stand 30.

FIGS. 5(*c*) and 5(*d*) are cross sectional views of the U-shaped member 11 of the arm rest device 10, obtained by cutting along the A—A dotted line in FIG. 5(*b*).

As shown in FIG. 5(*b*), a plurality of the first fasteners 42, 44 and 46 are provided on the base plate 16 of the U-shaped base member 11.

The fasteners 42 and 44 are provided in parallel to the side walls 12 in order to fix the arm rest pad members 22 and a transverse fastener 46 is provided to fix the head fixing member 23.

The respective arm rest pad member 22 and the head fixing member 23 have a mating fastener for interfitting to the fasteners 42, 44 or 46 in order to attach the respective member 22 at the appropriate positions.

FIG. 5(*d*) shows a preferable embodiment in which the inner surfaces of the U-shaped base member 12 are covered by a soft cushioning material 48, for example a urethane foam for supporting the patient's arms comfortably.

FIG. 5(*d*) further depicts another example of the projected leg member having a guiding groove 55 between the leg members 18 and 54 so as to interfit to a projected rail which is provided on the top surface of the table support stand 30.

Figure 6A:
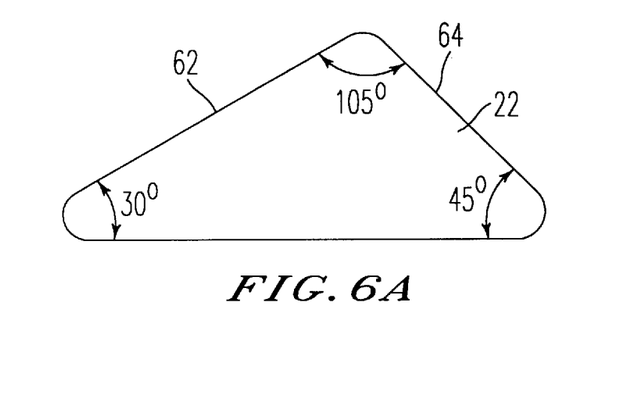
FIG. 6(a) is a cross sectional view of the triangle shaped mat portion of the patient's arm rest device.
Figure 6B:
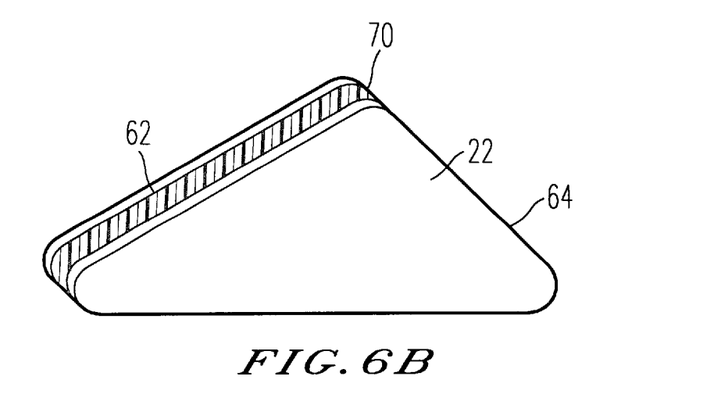
FIG. 6(b) is a perspective view of the triangle shaped mat portion of the patient's arm rest device, including a fastening means for fixing the mat portion at an optional position in the guide portion of the arm rest device.

FIGS. 6(a) and 6(b) depict one example of the shape of the arm rest pad member 22 for placing the U-shaped base member of the arm rest device 10.

As mentioned before, the arm rest pad member 22 has a suitable and changeable shape for supporting the patient arms, for example, a circular shape such as a pillow or a triangular shape as shown in FIGS. 6(a) and 6(b).

As shown in FIG. 6(a), the arm rest pad members 22 have a triangular shape for providing a plurality of different sloped surfaces for supporting the patient's upheld arms depending upon the patient's physical condition. The arm rest pad member of a triangular shape has at least two different internal angles for providing differently inclined arm supporting surfaces which can be used depending upon the patient's physical condition.

In FIGS. 6(a) and 6(b), the arm rest pad member 22 of triangular shape has three different internal angles for making three differently inclined arm support surfaces, one of which can be selected depending upon the patient's physical condition, the three internal angles being 30°, 45° and 110°, respectively, providing inclination surfaces 62 and 64 depending upon the patient's arm throwing condition.

The internal angle sizes of the arm rest pad member 22 were determined by human engineering testing as favorable for making the patient feel comfortable.

FIG. 6(b) shows an example of the triangular pad member 22 which is provided with a fastener means 70 on all three arm rest surfaces so as to selectively use all three surfaces.

FIGS. 7 through 10 illustrate various uses of the arm rest device 10.

Figure 7:
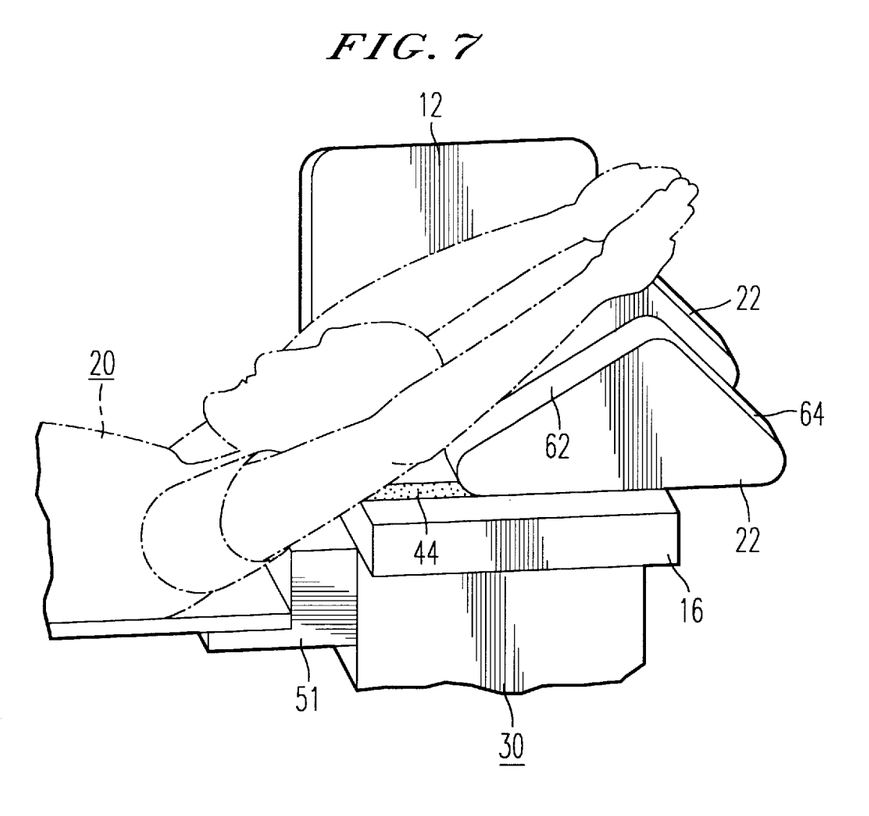
FIGS. 7 and 8 illustrate the different positions of patient arm rest facilitated by different faces of the triangle shaped mat having different inclination angles, respectively.
Figure 8:
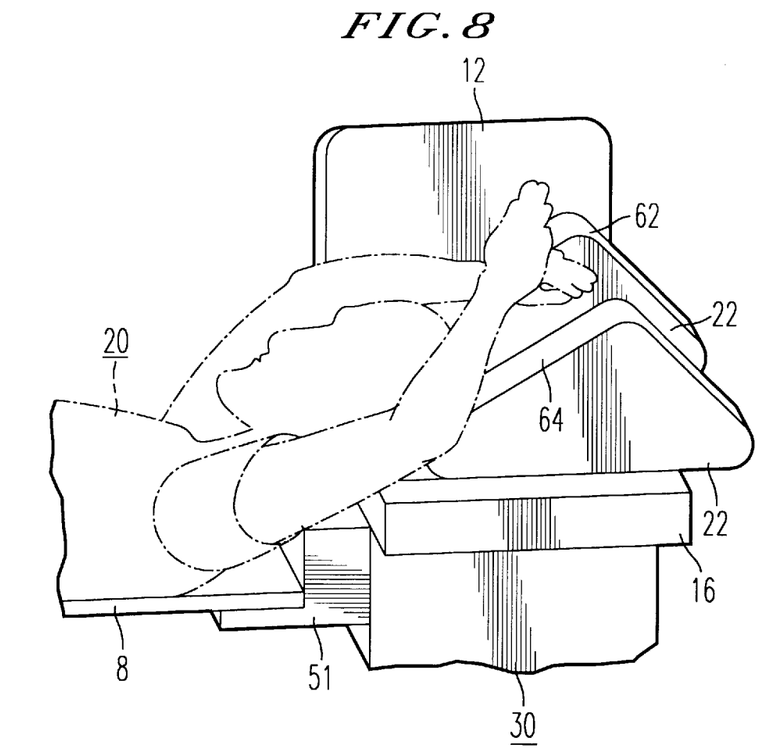

FIGS. 7 and 8 illustrate the different arm inclination angles can e obtained to support different positions of the patient's upheld arms.

In FIG. 7, the rest pad members 22 are attached to the fastener member 44 provided on the base plate 16 of the base member 11 so as to provide a small angle inclination surface for the arm rest device 10 so that the patient can throw his arms up almost straight beside his head. In this example, the internal angle of 30° of the pad member 22 as shown in FIG. 6(a) is used.

In FIG. 8, the pad members 22 are attached to the fastener member 44 provided on the base plate 16 of the base member 11 so as to provide a high angle inclination surface for the arm rest device 10 so that the patient hardly throws his arms up straight beside his head.

In these examples, the internal angle of 45° of the pad member 22 as shown in FIG. 6(a) is used and also the pad members 22 are attached as closely to the patient head possible.

Figure 9:
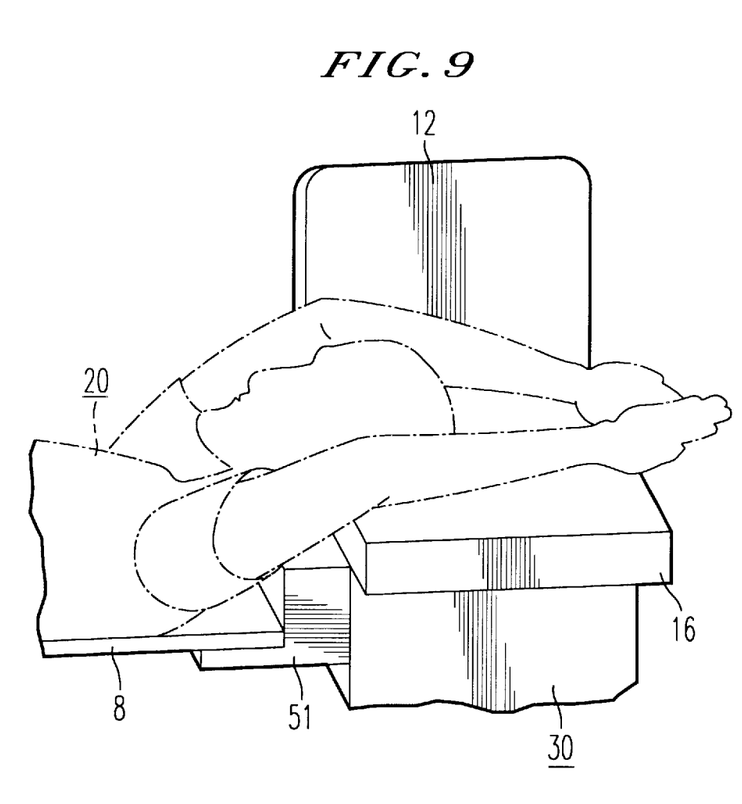
FIG. 9 depicts a use of the patient's arm rest device using only the guide portion without using mat portions.

FIG. 9 depicts use of the arm rest device with only the U-shaped base member 11 and without using the arm rest pad members 22.

Figure 10:
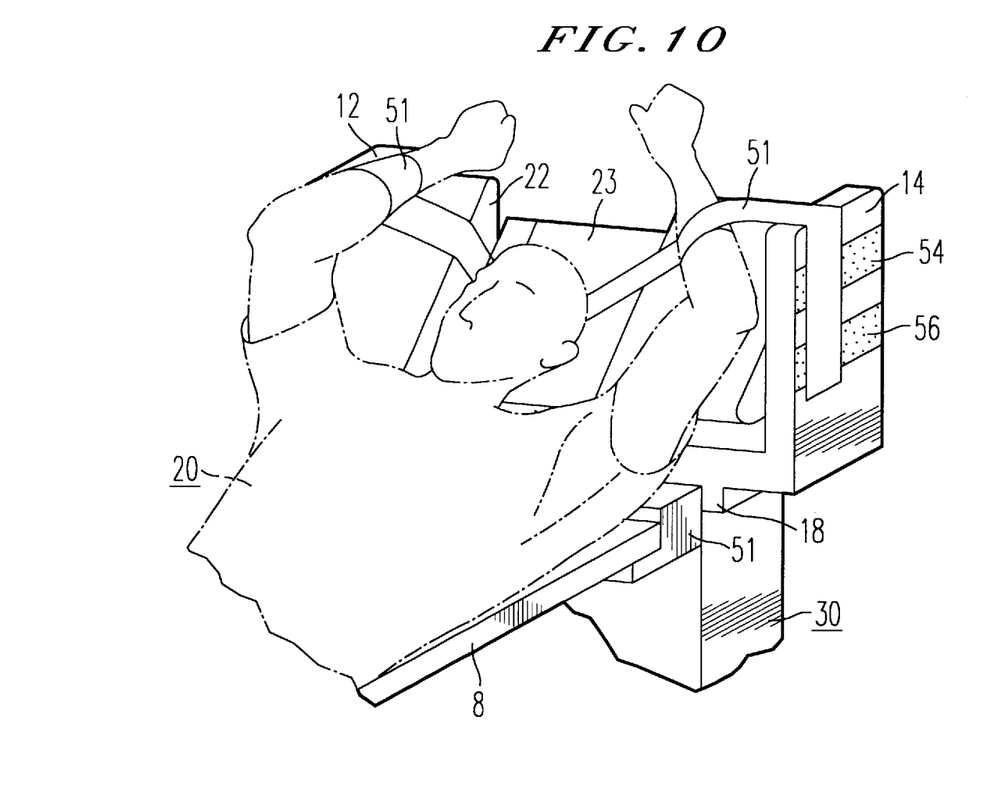
FIG. 10 is a perspective view illustrating another embodiment of the patient's arm rest device, including arms fixing means attached to the arm rest device.

FIG. 10 shows another embodiment of the arm rest device to which further includes an attachable hand fixing band member 51 for preventing the patient's arms movement during image diagnosis.

As explained before, if a patient moves during an image diagnosis investigation, it causes appearance of undesirable artifacts. So, in order to prevent the patient's movements during image diagnosis, an additional arm fixing band member 51 is additionally provided to the arm rest device 10.

As shown in FIG. 10, the attachable hand fixing band member 51 is made of a long strip fastener which can surround the patient's arms and can be fastened to the fastener tapes 54 and 56 provided on the outside surfaces of side walls 12 and 14.

It will be clear that the present invention is well adapted to carry out the objects and attain the ends and advantages mentioned as well as those inherent therein.

While a presently preferred embodiment has been described for purposes of this disclosure, numerous changes may be made which will readily suggest themselves to those skilled in the art and which are encompassed in the spirit of the invention disclosed and as defined in the appended claims.

What is claimed as new and desired to be secured by Letters Patent of the United States is:

1. An apparatus for image diagnosis, comprising:
a table on which a patient can be placed;
means for supporting the table;
means for detecting radiation emitted from a radiation source and passing through the patient in order to obtain a radioisotope distribution image of the patient;
means for carrying the detecting means to an examining position;
a detachable base guide disposed along one end of the table, the base guide including at least a base plate for attaching the base guide to the support means and a pair of side wall members extending upwardly above said base plate for supporting a patient's arms, said base plate having first and second sides spaced apart along a longitudinal axis of said table;
at least one arm rest pad member detachably provided on the base guide between the pair of the side wall members above said base plate, each arm pad member having a front side adjacent one of the first and second sides of the base plate and at least one surface inclined upwardly at an acute angle from said front side in a direction of the longitudinal axis of the table for supporting a patient's arms; and
a head rest detachably mounted on the base plate adjacent the at least one arm rest pad member, the head rest including at least a detachable head pad member for fixing a movement of the patient's head along a longitudinal axis of the table.

2. An apparatus for image diagnosis according to claim 1, wherein the base plate includes at least one fixing guide member for mounting the base guide on the table support means.

3. An apparatus for imaging diagnosis comprising:
a table on which a patient can be placed;
means for supporting the table;
detector means for detecting radiation emitted from a radiation source and passing through the patient in order to obtain a radioisotope distribution image of the patient;
means for carrying the detecting means to an investigating position; and
an arm rest device, including
a U-shaped base member mounted on the table supporting means and having a base plate and opposed side wall members interconnected by and extending above said base plate, said base plate having first and second sides spaced apart along a longitudinal axis of said table,
a detachable head rest member which provides a support surface for a patient's head and which is detachably placed in the U-shaped base member, and
at least one arm rest pad member detachably placed on said base plate between said side wall members adjacent said head rest member for providing support surfaces on which a patient's upheld arms can be rested during obtaining of said radioisotope distribution image, each arm pad member having a front side adjacent one of the first and second sides of the base plate and at least one surface inclined upwardly at an acute angle from said front side in a direction of a longitudinal axis of the table for supporting a patient's arms; and the head rest including at least a detachable head pad member for fixing a movement of the patient's head along the longitudinal axis of the table.

4. An apparatus for image diagnosis according to claims 1, 2 or 3, wherein:
each arm rest pad member has selectable support surfaces at different inclination angles.

5. An apparatus for image diagnosis according to claims 1, 2 or 3, wherein each arm rest pad member is at least partly made of a soft material.

6. An apparatus for image diagnosis according to claim 3, comprising:
fastener means for adjustably fixing the at least one arm rest pad member on the base plate member at selected positions.

7. An apparatus for image diagnosis according to claim 3, wherein:
the U-shaped base member includes a first fastener means on the base plate, and
each arm rest pad member has a second fastener means for interfitting with the first fastener means so as to fix the pad members adjustably on the base plate.

8. An apparatus for image diagnosis according to claim 3, wherein the U-shaped base member comprises:
a base plate which has a cut out portion for positioning the head rest member.

9. An apparatus for image diagnosis according to claim 3, wherein:
the arm rest device further comprises a pair of said arm rest pad members and a head fixing member between the pair of arm rest pad members so as to fix a patient's head into the head rest member, and
the base plate has an H-shaped fastener means for fixing both of the head fixing member and the pair of arm pad members.

10. An apparatus for image diagnosis according to claim 3, wherein:
the U-shaped base member includes a soft inner liner.

11. An apparatus for image diagnosis according to claim 3, wherein:
the arm rest device further includes an attachable hand fixing band member for preventing patient arm movement.

12. An apparatus for image diagnosis according to claim 4, wherein:
each of the pair of arm rest pad members h as a triangular cross sectional shape for selectable providing a plurality of differently sloped patient arm support surfaces.

13. An apparatus for image diagnosis according to claim 7, wherein:
the first and second fastener means are each made of a fastener tape for interfitting with each other.

14. An apparatus for image diagnosis according to claim 8, wherein:
the head rest member has a depression for support of a patient's head.

15. An apparatus for image diagnosis according to claim 9, wherein:
the head fixing member and the pair of arm rest pad members are comprised of a U-shaped one piece member.

16. An apparatus for image diagnosis according to claim 11, wherein:
the attachable hand fixing band member is made of a strip fastener sufficiently long so as to be able to surround the patient's arms and be fastened to side walls of the U-shaped base member.

17. An apparatus for image diagnosis according to claim 12, wherein:
each of the arm rest pad members of a triangular cross sectional shape has at least two different internal angles for making differently inclined arm support surfaces which can be selected as desired.

18. An apparatus for image diagnosis according to claim 17, wherein:
each of the arm rest pad members of a triangular cross sectional shape has three different internal angles for selectable providing three differently inclined arm support surfaces.

19. An apparatus for image diagnosis according to claim 14, wherein:
at least the depression of the head rest member is made of a urethane foam.

20. An apparatus for image diagnosis according to claim 18, wherein:
the three degrees of the respective internal angles of the arm rest pad members of triangular cross sectional shape are 30°, 450° and 105°.

21. A scintillation camera apparatus for image diagnosis, comprising:
a plate table on which a patient can be placed;
a pair of means for supporting and elevating the plate table;
means for detecting y-ray radiations emitted from a radioactive isotope investigator injected into the patient and passing through the patient in order to obtain a radioisotope distribution image of the patient;
means for supporting and positioning the detecting means at an image diagnosis position;
a detachable base guide disposed along one end of the table, the base guide including at least a base plate for attaching the base guide to the support means and a pair of side wall members extending above the base plate, said base plate having first and second sides spaced apart along a longitudinal axis of said table;
at least one arm rest pad member detachably provided on the base guide above said base plate and between the pair of the side wall members, each arm pad member having a front side adjacent one of the first and second sides of the base plate and at least one surface inclined upwardly at an acute angle from said front side in a direction of a longitudinal axis of the table for supporting a patient's arms; and
a head rest detachably mounted on the base plate adjacent the at least one arm rest pad member, the head rest including at least a detachable head pad member for fixing a movement of the patient's head along the longitudinal axis of the table.

22. A computer tomography apparatus for image diagnosis, comprising:
a plate table on which a patient can be placed;

a pair of means for supporting the plate table;

means for detecting X-rays penetrated through the patient in order to obtain a radioisotope distribution image of the patient;

means for supporting and positioning the detecting means at an image diagnosis position;

a detachable base guide disposed along one end of the table, the base guide including at least a base plate for attaching the base guide to the support means and a pair of side wall members connected by said base plate and extending above the base plate, said base plate having first and second sides spaced apart along a longitudinal axis of said table;

at least one arm rest pad member detachably provided on the base guide above the base plate between the pair of the side wall members, each arm pad member having a front side adjacent one of the first and second sides of the base plate and at least one surface inclined upwardly at an acute angle from said front side in a direction of the longitudinal axis of the table for supporting a patient's arms; and a head rest detachably mounted on the base plate adjacent the at least one arm rest pad, the head rest including at least a detachable head pad member for fixing a movement of the patient's head along the longitudinal axis of the table.

23. A nuclear magnetic resonance apparatus for image diagnosis, comprising:

a plate table on which a patient can be placed;

means for supporting the plate table;

means for detecting magnetic resonance from an investigation part through the patient in order to obtain a radioisotope distribution image of the patient;

means for supporting and positioning the detecting means at an image diagnosis position;

a detachable base guide disposed along one end of the table, the base guide including at least a base plate for attaching the base guide to the support means and a pair of side wall members connected by said base plate and extending above the base plate, said base plate having first and second sides spaced apart along a longitudinal axis of said table;

at least one arm rest pad member detachably provided on the base guide above the base plate between the pair of the side wall members, each arm pad member having a front side adjacent one of the first and second sides of the base plate and at least one surface inclined upwardly at an acute angle from said front side in a direction of the longitudinal axis of the table for supporting a patient's arms; and a head rest detachably mounted on the base plate adjacent the at least one arm rest pad member, the head rest including at least a detachable head pad member for fixing a movement of the patient's head along the longitudinal axis of the table.

24. An apparatus for image diagnosis according to claims 21, 22 or 23, wherein:

the base plate has guide members for mounting on the one of the table supporting means.

25. An apparatus for image diagnosis according to claim 24, wherein:

the arm rest pad members have selectable support surfaces at different inclination angles.

26. An apparatus for image diagnosis according to claim 24, wherein the base guide comprises:

fastener means for adjustably positioning the pair of arm rest pad members on the base plate.

27. An apparatus for image diagnosis according to claim 24, wherein:

the base guide has a first fastener means on the base plate, and each arm rest pad member has a second fastener means for intermitting with the first fastener means so as to fix the pad members adjustably on the base plate.

28. An apparatus for image diagnosis according to claim 24, wherein:

each of the pair of arm rest pad members has a triangular cross sectional shape for selectable providing a plurality of different sloped patient arm support surfaces.

29. An apparatus for image diagnosis according to claim 28, wherein:

each of the arm rest pad members of triangular cross sectional shape has at least two different internal angles for making differently inclined arm support surfaces which can be selected as desired.

30. An apparatus for image diagnosis according to claim 24, wherein:

each of the arm rest pad members of triangular cross sectional shape has three different internal angles for support surfaces.

31. An apparatus for image diagnosis according to claim 24, wherein:

the base plate has a cut out portion for positioning the head rest.

32. An apparatus for image diagnosis according to claim 24, wherein:

the arm rest device includes a pair of arm rest pad members provided on opposed sides of said head rest, and the base guide further includes a head fixing member between the pair of arm rest pad members so as to fix a patient's head into the head rest, and the base plate has an H-shaped fastener means for fixing both of the head fixing member and the pair of arm pad members.

33. An apparatus for image diagnosis according to claim 24, wherein:

the base guide includes a soft inner liner.

34. An apparatus for image diagnosis according to claim 24, wherein:

the base guide further includes an attachable hand fixing band member for preventing-patient arm movement.

35. An apparatus for image diagnosis according to claim 27, wherein:

the first and second fastener means are each made of a fastener tape for interfitting with each other.

36. An apparatus for image diagnosis according to claim 31, wherein:

the head rest has a depression for support of the patient's head.

37. An apparatus for image diagnosis according to claim 32, wherein:

the head fixing member and the pair of arm rest pad members are made of a U-shaped one piece member.

38. An apparatus for image diagnosis according to claim 34, wherein:

the attachable hand fixing band member is made of a strip fastener sufficiently long so as to be able to surround the patient's arms and be fastened to side wall members of the base guide.

39. An apparatus for image diagnosis according to claim 36, wherein:
at least the depression part of the head rest is made of urethane foam.

40. An apparatus according to claim 5, wherein the at least one arm rest pad member at least partially includes urethane foam.

41. An apparatus according to claim 10, wherein the inner lining of the U-shaped base member at least partially is made of urethane foam.

42. An apparatus according to claim 31, wherein the soft inner liner of the U-shaped base member is made at least partially of urethane foam.

* * * * *